United States Patent
Sharratt

[19]

[11] Patent Number: 5,882,298

[45] Date of Patent: Mar. 16, 1999

[54] RETRACTOR ASSEMBLY WITH CONNECTING PIN AND METHOD FOR REMOVABLY ASSEMBLING

[75] Inventor: Todd W. Sharratt, Cottage Grove, Minn.

[73] Assignee: Minnesota Scientific, Inc., Minneapolis, Minn.

[21] Appl. No.: 129,242

[22] Filed: Aug. 5, 1998

[51] Int. Cl.⁶ ................................................ A61B 17/00
[52] U.S. Cl. ............................................ 600/213; 600/210
[58] Field of Search ............................ 600/201, 210, 600/213, 226, 227, 234

[56] References Cited

U.S. PATENT DOCUMENTS

| | | | |
|---|---|---|---|
| 569,839 | 10/1896 | Roeloffs | 600/213 |
| 2,850,008 | 9/1958 | Resch. | |
| 3,467,079 | 9/1969 | James. | |
| 3,522,799 | 8/1970 | Gauthier. | |
| 3,724,449 | 4/1973 | Gauthier. | |
| 4,337,762 | 7/1982 | Gauthier. | |
| 4,616,390 | 10/1986 | MacCracken | 29/157.3 |
| 4,617,916 | 10/1986 | LeVahn et al. | 600/228 |
| 4,834,112 | 5/1989 | Machek et al. | 600/237 X |
| 4,934,352 | 6/1990 | Sullivan, Jr. | 600/213 |
| 5,352,220 | 10/1994 | Abidin et al. | 600/226 X |
| 5,503,617 | 4/1996 | Jako | 600/201 |
| 5,520,608 | 5/1996 | Cabrera et al. | 600/201 |
| 5,529,358 | 6/1996 | Dinkler et al. | 600/233 |
| 5,688,223 | 11/1997 | Rosendahl | 600/215 |
| 5,705,014 | 1/1998 | Schenck et al. | 156/272.4 |
| 5,795,291 | 8/1998 | Koros et al. | 600/213 X |

OTHER PUBLICATIONS

J.F. Schenck, *The Role of Magnetic Susceptbility in Magnetic Resonance Imaging: MRI Magnetic Compatibility of the First and Second Kinds*, Medical Physics, vol. 23, No. 6, Jun. 1996, pp. 815–850.

*Primary Examiner*—Jeffrey A. Smith
*Attorney, Agent, or Firm*—Kinney & Lange, P.A.

[57] ABSTRACT

A surgical retractor assembly includes a handle and a retractor blade connected to the handle by a connecting pin. The connecting pin has a handle-connecting portion that extends through an aperture in the handle and a blade-connecting portion with spaced-apart flanges separated by a blade engaging portion that engages a slot in the retractor blade.

15 Claims, 3 Drawing Sheets

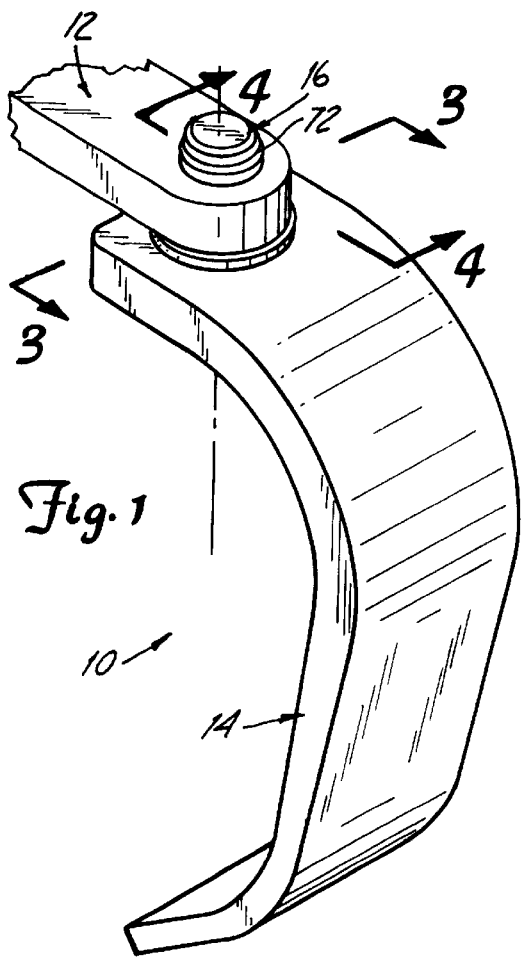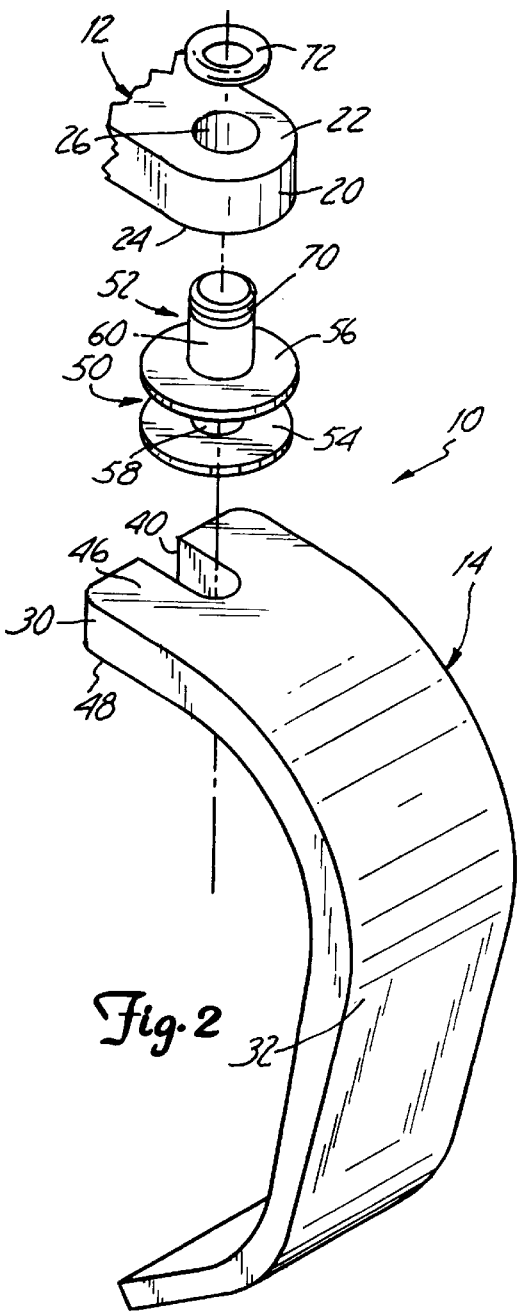

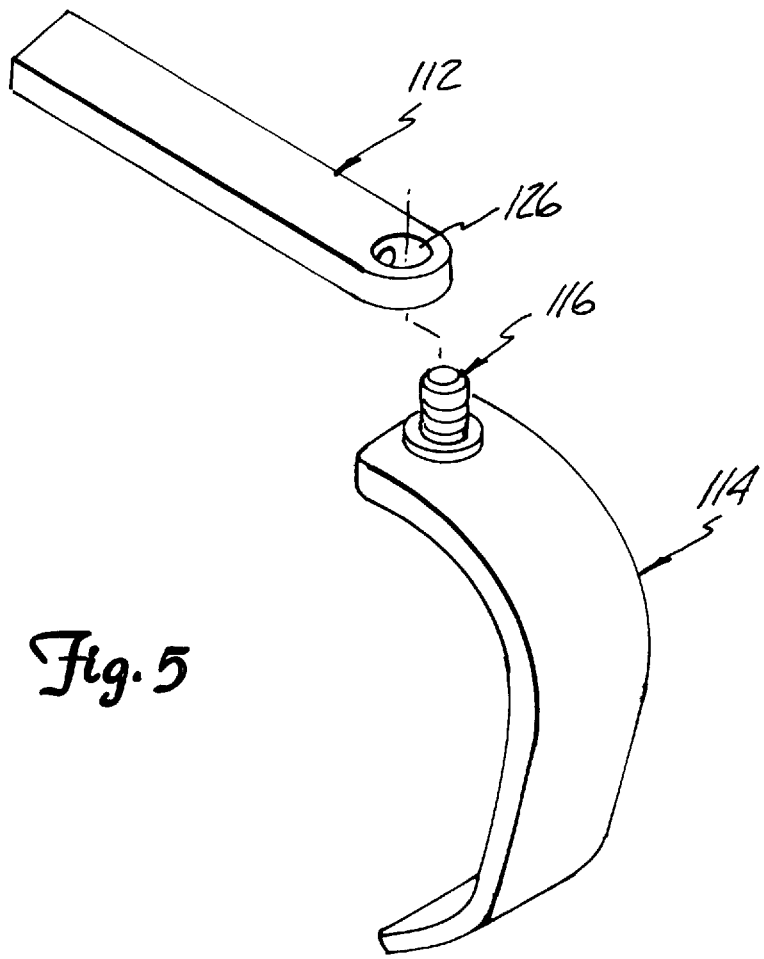
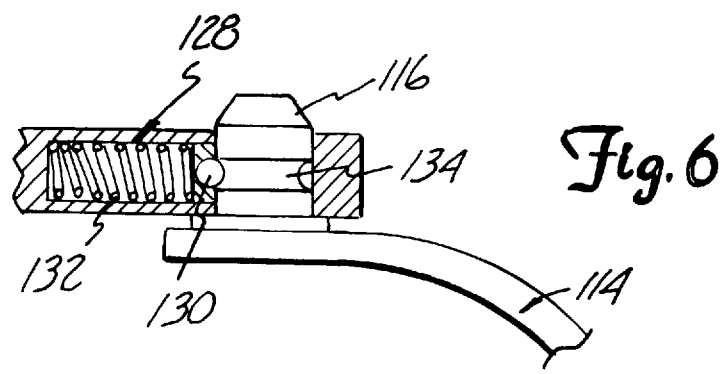

RETRACTOR ASSEMBLY WITH CONNECTING PIN AND METHOD FOR REMOVABLY ASSEMBLING

BACKGROUND OF THE INVENTION

The present invention relates generally to surgical retractors. More particularly, the present invention relates to a retractor assembly for use with magnetic resonance imaging (MRI).

During the last two decades MRI has become a popular diagnostic technique because this technique enables details of images to be obtained inside of a human body. Advantages of MRI over other diagnostic techniques are that MRI does not require the use of x-ray radiation. Additionally, for most applications, patients do not need to perform or refrain from performing any activities prior to undergoing a MRI session.

Because of the beneficial features of MRI, MRI has been attempted while performing selected surgical techniques. A drawback of using MRI while performing surgical techniques is that metal objects present in the area where the image is being taken and that have a magnetic susceptibility cause distortion of the image.

During many types of surgical techniques it is desirable to use retractors to retract tissue and thereby enhance the surgeon's ability to perform the surgical technique. Most present surgical retractors are made of stainless steel which is a highly magnetic susceptible metal.

BRIEF SUMMARY OF THE INVENTION

The present invention includes a surgical retractor assembly that is particularly suitable for use with MRI. The assembly includes a handle, and a retractor blade connected to the handle by a connecting pin. The retractor blade may be made of a MRI compatible material.

The connecting pin has a handle-connecting portion that extends through an aperture in the handle and a blade-connecting portion with spaced-apart flanges separated by a blade engaging portion that engages a slot in the retractor blade.

BRIEF DESCRIPTION OF THE DRAWINGS

FIG. 1 is a perspective view of a retractor assembly according to the present invention.

FIG. 2 is an exploded view of the retractor assembly.

FIG. 5 is an exploded view of an alternative embodiment of a retractor assembly according to the present invention.

FIG. 6 is a sectional view of the retractor assembly of FIG. 5.

DETAILED DESCRIPTION

Figure 3:
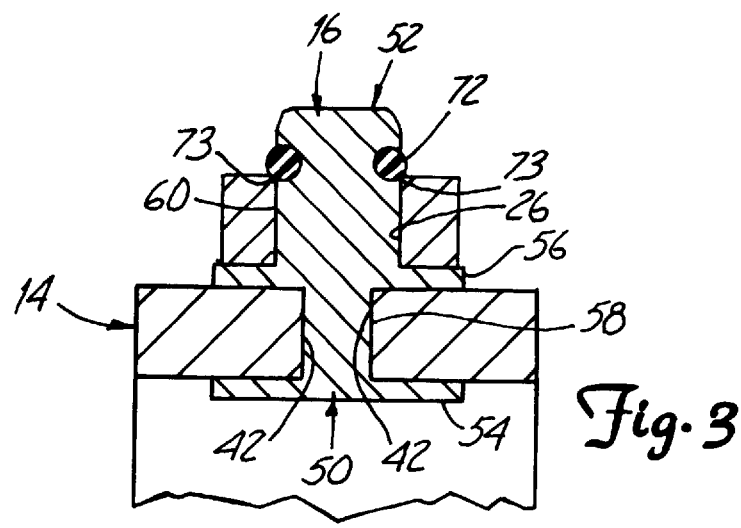
FIG. 3 is a sectional view of the retractor assembly taken along a line 3—3 in FIG. 1.

The present invention includes a retractor assembly, as most clearly illustrated at 10 in FIGS. 1 and 2. The retractor assembly 10 is particularly suited for use in performing surgical techniques where the progress of the surgical technique is monitored with MRI. Portions of the assembly are made of material that has a minimal magnetic susceptibility so that image disturbances or distortions are minimized.

Materials that have minimal magnetic susceptibility and are suitable for use in surgical procedures that are monitored using MRI are well-known. Many such materials are listed in *The Role of Magnetic Susceptibility in Magnetic Resonance Imaging: MRI Magnetic Compatibility of the First and Second Kinds*, Med. Phys. 23(6), pages 815–850, June 1996, which is herein incorporated by reference. Such materials include the following: carbon fiber composites, wood, copper, aluminum, brass, lead, zinc, titanium, molybdenum, tungsten, tantalum, zirconium, bismuth, nylon, teflon, polysulfon and most other synthetic polymers.

For purposes of this application, magnetic susceptibility is a measure of a material's tendency to interact with and distort an applied magnetic field. If a material distorts such a field, it will then distort or degrade the image being produced by MRI since such imaging depends on the magnetic field. The extent of image distortion or degradation that can be tolerated depends on the procedure.

The retractor assembly 10 includes a retractor handle 12, a retractor blade 14, and a connecting pin 16 that operably connects the retractor handle 12 and the retractor blade 14. At least the retractor blade 14 of the retractor assembly 10 is preferably fabricated from a MRI compatible material such as a synthetic polymer. For most uses of the assembly 10, the retractor handle may be made of a magnetically susceptible material such as stainless steel since the MRI field will be directed in an area that will exclude the handle.

One advantage of the present invention is that the configuration of the connecting pin 16 securely connects a retractor blade made of a synthetic polymer to a stainless steel handle. In addition, the pin enables the retractor blade 14 to be readily attached to and disengaged from the retractor handle 12. Readily changing the retractor blade 14 while performing a surgical technique is desirable when performing many surgical techniques that require different retractor blades to be used at selected times during the surgical technique.

At least an end portion 20 of the retractor handle 12 preferably has a substantially rectangular profile with an upper surface 22 and a lower surface 24. The end portion 20 has an aperture 26 formed therein. The aperture 26 has a selected diameter and extends through the portion 20 between the upper surface 24 and the lower surface 26. The diameter of the aperture 26 in one embodiment is preferably approximately 0.35 inches.

The retractor blade 14 has a main body 32 with a proximal end portion 30. The main body 32 is formed with a selected width and curvature depending on the surgical procedure in which it is desired to use the retractor blade 14. Typically, such retractor blades have been made of stainless steel. The retractor blade 14 is preferably fabricated from a material that is compatible with MRI. The material used to fabricate the retractor blade 14 must also be durable so that the retractor blade 14 does not degrade during repeated uses and sterilization cycles. Such materials generally include synthetic polymers that have characteristics which when fabricated into a retractor blade have similar strength characteristics as a stainless steel retractor blade. In addition, the polymer must withstand repeated sterilization cycles. One suitable polymer is a polyetherimide sold under the trademark ULTEM 1000 by General Electric Company of Pittsfield, Mass.

Figure 4:
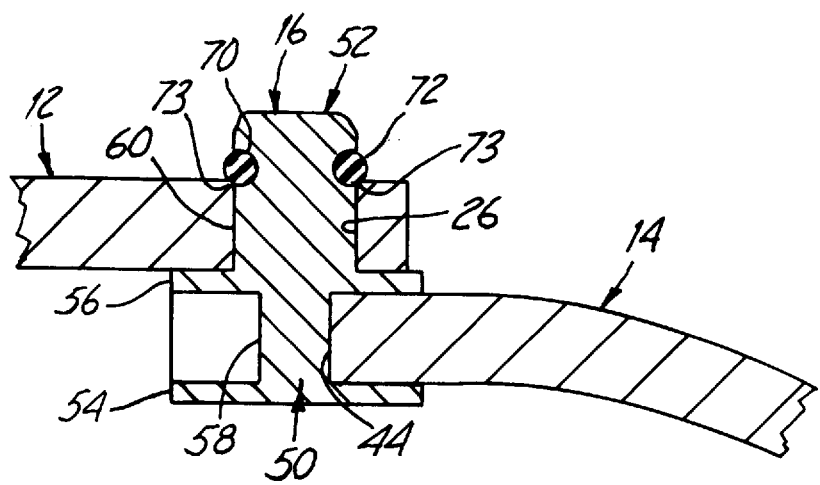
FIG. 4 is a sectional view of the retractor assembly taken along a line 4—4 in FIG. 1.

The end portion 30 has a top surface 46 and a lower surface 48, as most clearly illustrated in FIGS. 3 and 4. A distance between the upper surface 46 and the lower surface 48 in one embodiment is preferably about 0.25 inches. The end portion 30 includes a slot 40 formed therein. The slot 40 extends between the top surface 46 and the lower surface 48 and is defined by a pair of side walls 42 and an end wall 44 that extends between the side walls 42. The side walls 42 are preferably substantially parallel to each other and are spaced-apart a selected distance. The end wall 44 preferably has a semi-cylindrical shape, as illustrated in FIG. 2.

The connecting pin 16 includes a retractor blade engaging portion 50 and a retractor handle engaging portion 52, as illustrated in FIGS. 2–4. The retractor blade engaging portion 50 includes a first flange 54, and a second flange 56, and a cylindrical section 58 that extends between the first flange 54 and the second flange 56. A diameter of the first flange 54 and the second flange 56 in one embodiment are each preferably about 0.67 inches.

The connecting pin 16 is preferably fabricated from a material that does not interfere with MRI. However, the material used to fabricate the connecting pin 16 must be sufficiently durable so that the connecting pin 16 does not degrade over repeated uses and sterilization cycles. A preferred material for fabricating the connecting pin 16 is a metal such as titanium.

For those situations that in which MRI imaging is not used, the pin of the present invention is useful in securing retractor blades made of stainless steel to the handle 12. The pin in this case is also made of stainless steel.

A spacing between the first flange 54 and the second flange 56 is preferably approximately the same as the thickness (distance between the top surface 42 and the lower surface 44) of the end portion 32 of the retractor blade 14. The spacing between the first flange 54 and the second flange 56 in one embodiment is preferably approximately 0.25 inches. Since the spacing between the first and second flanges 54 and 56 is the same as the thickness of the end portion 30, the end portion 30 is frictionally retained between the flanges.

A height of the cylindrical section 58 is approximately the same as the distance that the side walls 42 are spaced-apart, as illustrated in FIG. 3. The height of the cylindrical section 58 of one embodiment is preferably 0.19 inches. Additionally, the semi-cylindrical shape of the end wall 44 conforms to the cylindrical portion 58 and is substantially adjacent to the end wall 44 when the connecting pin 16 is attached to the retractor blade 14, as illustrated in FIG. 4. Frictional contact between the side walls 42, the end wall 44, and the cylindrical portion 58 further assist in frictionally attaching the pin 16 with the retractor blade 14.

The retractor handle engaging portion 52 includes a cylindrical section 60 that extends from the second flange 56. A diameter of the cylindrical section 60 is approximately the same as a diameter of the aperture 26. The diameter of the cylindrical section 60 in one embodiment is preferably approximately 0.33 inches.

The cylindrical section 60 includes an annular channel 70. The channel 70 is spaced from the second flange 56 approximately the same as the distance between the upper surface 22 and the lower surface 24 of the retractor handle 12. The spacing between the channel 70 and the second flange 56 in one embodiment is approximately 0.24 inches.

An O-ring 72 is partially seated within the channel 70 with a portion extending beyond the channel 70. In addition, the channel 70 is positioned such that the O-ring 72 impinges on an adjacent circumferential corner edge 73 of the aperture 26. The O-ring 72 is preferably fabricated from a compressible material such as a hard rubber to permit the O-ring 72 to impinge upon the corner edge 73 thereby providing a secure attachment of the pin to the handle 12.

In operation, the retractor handle 12 is fixedly mounted in a desired position with respect to an area where the surgical technique is to be performed. One such device for mounting the retractor handle 12 is disclosed in LeVahn et al., U.S. Pat. No. 4,617,916, which is assigned to the assignee of the present application and is hereby incorporated by reference.

To connect the retractor handle 12 with the connecting pin 16, the aperture 26 is positioned adjacent the pin 16, and the connecting pin 16 is urged through the aperture 26 until the O-ring 72 extends through the aperture 26.

The retractor blade 14 is attached to the connecting pin 16 by positioning the cylindrical section 60 adjacent the slot 40 and then urging the connecting pin 16 toward the retractor blade 14 until the cylindrical section 60 is substantially adjacent the end wall 44. As the cylindrical section 60 engages the end wall 44, the two surfaces snap fit in frictional engagement. As noted above, frictional contact between the first flange 54, the second flange 56, and the end portion 30 retains the retractor blade 14 with respect to the connecting pin 16. Additionally, frictional contact between the cylindrical section 60, the side walls 42, and the end wall 44 further aid in retaining the retractor blade 14 with respect to the connecting pin 16.

When it is desired to change the retractor blade 14 that is attached to the retractor handle 12, the retractor blade 14 is simply pulled away from the retractor handle 12 until the handle 12 and the pin 16 are disengaged. A differently shaped retractor blade 14 may be attached to the retractor handle 12 using the technique described above.

In an alternative embodiment, as illustrated in FIGS. 5 and 6, the retractor blade 114 is attached to the retractor handle 112 through a connecting pin 116 that engages an aperture 126 in the retractor handle and is held therein by a detent mechanism 128, as best illustrated in FIG. 6. The detent mechanism 128 includes a ball 130 biased in a direction towards the connecting pin 116 by a spring 132. The ball 130 extends partially into the aperture 126. The ball 130 engages a groove 134 in the connecting pin 116 to retain the connecting pin 116 within the aperture 126 thereby connecting the retractor blade 114 to the handle 112.

To engage the retractor blade 114 to the handle 112, the connecting pin is inserted within the aperture 126. As the pin is inserted into the aperture 126, the spring biased ball 130 is pushed back against the spring 132, and when the connecting pin 116 is positioned to be locked, the groove 134 is disposed adjacent the ball 130 wherein the ball 130 engages the groove 134 to lock the connecting pin 116 in place. To disengage the retractor blade 114 from the retractor handle 112, the blade is pulled away from the handle 112 thereby pushing the ball 130 back against the spring 132 so that the connecting pin 116 is removed from the aperture 126.

Although the present invention has been described with reference to preferred embodiments, workers skilled in the art will recognize that changes may be made in form and detail without departing from the spirit and scope of the invention.

I claim:

1. A surgical retractor assembly comprising:
   a handle having an aperture of a selected diameter;
   a retractor blade having a slot formed therein; and
   a connecting pin having a handle-engaging portion extending through the aperture and a slot-engaging portion with spaced-apart flanges separated by a blade engaging portion disposed within the slot.

2. The surgical retractor assembly of claim 1 wherein the retractor blade is fabricated from an MRI compatible material.

3. The surgical retractor assembly of claim 1 wherein the spaced-apart flanges frictionally engage surfaces proximate the slot to retain the retractor blade.

4. The surgical retractor assembly of claim 1 wherein the slot is defined by a pair of side walls and an end wall and wherein the slot-engaging portion of the connecting pin is in frictional engagement with the pair of side walls and the end wall.

5. The surgical retractor assembly of claim 1 wherein the handle-engaging portion includes an annular channel formed therein.

6. The surgical retractor assembly of claim 5, and further comprising a compressible ring seated within the channel and impinging on the surface adjacent the aperture.

7. The surgical retractor assembly of claim 1 wherein the retractor blade is made of an MRI compatible material and the handle is made of a magnetically susceptible material.

8. A surgical retractor assembly comprising:
   a handle having an aperture formed therein;
   a retractor blade having a selected thickness and a slot formed therein;
   a compressible ring;
   a connecting pin comprising:
      a handle-connecting portion with a channel formed therein, wherein the channel is adapted to receive the compressible ring; and
      a blade-connecting portion comprising a pair of spaced-apart flanges separated by a blade engaging section wherein a spacing between the flanges is approximately the same as a thickness of the retractor blade proximate the slot so that the flanges frictionally engage the retractor blade.

9. The surgical retractor assembly of claim 8 wherein the retractor blade is fabricated from an MRI compatible material.

10. The surgical retractor assembly of claim 8 wherein the compressible ring impinges upon the surface of the handle adjacent the aperture.

11. A method for removably attaching a retractor blade to a handle with a connecting pin, wherein the handle has an aperture of a selected diameter, wherein the retractor blade has a slot formed therein, and wherein the connecting pin has a handle-connecting portion and a blade-connecting portion with spaced-apart flanges separated by a blade engaging portion with a selected width, the method comprising:
   extending the handle-connecting portion through the aperture to attach the connecting pin to the handle; and
   urging the blade-connecting portion into the slot to attach the connecting pin to the retractor blade.

12. The method of claim 11 wherein the spaced-apart flanges frictionally engage upper and lower surfaces of the retractor blade proximate the slot.

13. The method of claim 11 wherein the blade engaging portion frictionally engages side walls and an end wall that define the slot.

14. The method of claim 11, and further comprising forming an annular channel in the handle-connection portion wherein the connecting pin is retained in engagement with the handle by a compressible ring that is at least partially seated in the channel.

15. A surgical retractor assembly comprising:
   a handle having an aperture formed therein;
   a retractor blade;
   a connecting pin connected to one end of the retractor blade and extending therefrom;
   a detent mechanism including a spring biased ball extending partially into the aperture and a detent ball engaging groove disposed on the connecting pin such that when the connecting pin is inserted into the aperture, the ball engages the groove.

* * * * *